(12) United States Patent
DePinho

(10) Patent No.: US 6,297,368 B1
(45) Date of Patent: Oct. 2, 2001

(54) MYC HOMOLOGY REGION II—ASSOCIATED PROTEIN AND USES THEREOF

(75) Inventor: Ronald A. DePinho, Brookline, MA (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/497,779

(22) Filed: Feb. 3, 2000

Related U.S. Application Data

(63) Continuation-in-part of application No. 08/946,692, filed on Oct. 8, 1997, now Pat. No. 6,040,425.
(51) Int. Cl.⁷ .......................... C07H 21/04; C07K 14/47
(52) U.S. Cl. ..................... 536/23.5; 530/350; 530/300; 530/827; 514/12
(58) Field of Search .................. 536/23.1, 23.5; 530/350

(56) References Cited

U.S. PATENT DOCUMENTS 6,040,425 * 3/2000 DePinho .............................. 530/350

OTHER PUBLICATIONS

DePinho, R, et al, 1987, Myc family of cellular oncogenes, Journal of Cellular Biochemistry, vol. 33, pp. 257–266.*
Schreiber–Agus, N, et al, 1997, A biochemical and biological analysis of myc superfamily interactions, Current Topics in Immunology.*
FitzGerald, MJ, et al, 1999, Differential effects of the widely expressed dMax splice variant of Max on E–box vs initiator element–mediated regulation by c–Myc, Oncogene, vol. 18, pp. 2489–2498.*
Schreiber–Agus, N, et al, 1998, Repression by the Mad(Mxi1)–Sin3 complex, Bioessays, vol. 20, pp. 808–818.*

* cited by examiner

*Primary Examiner*—Donna C. Wortman
*Assistant Examiner*—Stephen Rawlings
(74) *Attorney, Agent, or Firm*—Amster, Rothstein & Ebenstein

(57) ABSTRACT

The present invention provides a novel MHRII-associated protein designated MHRII-AP62 and antibodies immunoreactive with the MHRII-AP62 protein. Also provided are kits containing these antibodies and methods of using the antibodies for the detection of the MHRII-AP62 protein. The present invention also provides for a nucleic acid encoding the MHRII-AP62 protein and nucleic acid probes for use in the detection of the MHRII-AP62 protein. Further provided by the present invention are agents that mimic the activity of the MHRII-AP62 protein by binding to the MHRII, agents that inhibit the activity of the MHRII-AP62 protein by binding to the MHRII-AP62 protein, or by binding to the nucleic acid encoding the MHRII-AP62 protein, and methods of using these agents to treat cancer and cancer causing diseases.

2 Claims, 15 Drawing Sheets cctcgagagt tcacatcaga gattgttaca gagggaaaac agaagaggtc atcaccacct
catttacaga agataacaaa gttgttaact gtaaagtcag aggatgttct tgctcagtca
ccattgtcca aactcagagg ctcagaatgc tggtggacaa gaagcctaag aaataaagtc
atctgtctag accacaaaaa accaaaagct gcccgtgggt gtcctcctaa gggattacca
aaaaggcatc tcagagttat gttgacgaat gttctatgga cggacttagg acgagaattc
agaaagaccc tgcctagaaa ggatgctaat ttat

FIG. 7A

Pro Arg Glu Phe Thr Ser Glu Ile Val Thr Glu Gly Lys Gln Lys Arg Ser
Ser Pro Pro His Leu Gln Lys Ile Thr Lys Leu Leu Thr Val Lys Ser Glu
Asp Val Leu Ala Gln Ser Pro Leu Ser Lys Leu Arg Gly Ser Glu Cys Trp
Trp Thr Arg Ser Leu Arg Asn Lys Val Ile Cys Leu Asp His Lys Lys Pro
Lys Ala Ala Arg Gly Cys Pro Pro Lys Gly Leu Pro Lys Arg His Leu Arg
Val Met Leu Thr Asn Val Leu Trp Thr Asp Leu Gly Arg Glu Phe Arg Lys
Thr Leu Pro Arg Lys Asp Ala Asn Leu

FIG. 7B

```
8A        CGCCCGGGCAGGTAGAAGATGGACAGGGCCAGGCCTGGGCGTCGGCGAGCTTCATCAGAG
       1  ---------+---------+---------+---------+---------+---------+  60
          GCGGGCCCGTCCATCTTCTACCTGTCCCGGTCCGGACCCGCAGCCGCTCGAAGTAGTCTC

8B                  M  D  R  A  R  P  G  R  R  R  A  S  S  E    -

8A        ATTGTTACAGAGGGAAAACAGAAGAGGTCATCACCACCTCATTTACAGAAGATAACAAAG
      61  ---------+---------+---------+---------+---------+---------+ 120
          TAACAATGTCTCCCTTTTGTCTTCTCCAGTAGTGGTGGAGTAAATGTCTTCTATTGTTTC

8B         I  V  T  E  G  K  Q  K  R  S  S  P  P  H  L  Q  K  I  T  K   -

8A        TTGTTAACTGTAAAGTCAGAGGATGTTCTTGCTCAGTCACCATTGTCCAAACTCAGAGGC
     121  ---------+---------+---------+---------+---------+---------+ 180
          AACAATTGACATTTCAGTCTCCTACAAGAACGAGTCAGTGGTAACAGGTTTGAGTCTCCG

8B         L  L  T  V  K  S  E  D  V  L  A  Q  S  P  L  S  K  L  R  G   -

8A        TCAGAATGCTGGTGGACAAGAAGCCTAAGAAATAAAGTCATCTGTCTAGACCACAAAAAA
     181  ---------+---------+---------+---------+---------+---------+ 240
          AGTCTTACGACCACCTGTTCTTCGGATTCTTTATTTCAGTAGACAGATCTGGTGTTTTTT

8B         S  E  C  W  W  T  R  S  L  R  N  K  V  I  C  L  D  H  K  K   -

8A        CCAAAAGCTGCCCGTGGGTGTCCTCCTAAGGGATTACCAAAAAGGCATCTCAGAGTTATG
     241  ---------+---------+---------+---------+---------+---------+ 300
          GGTTTTCGACGGGCACCCACAGGAGGATTCCCTAATGGTTTTTCCGTAGAGTCTCAATAC

8B         P  K  A  A  R  G  C  P  P  K  G  L  P  K  R  H  L  R  V  M   -

8A        TTGACGAATGTTCTATGGACGGACTTAGGACGAgaattcAGAAAGACCCTGCCTAGAAAG
     301  ---------+---------+---------+---------+---------+---------+ 360
          AACTGCTTACAAGATACCTGCCTGAATCCTGCTcttaagTCTTTCTGGGACGGATCTTTC

```
8A         GATGCTAATTTATGTGCTCCCAGCAAGGTGCAATCAGACTCATTGCCTTCGACATCTGTT
     361   ---------+---------+---------+---------+---------+---------+ 420
           CTACGATTAAATACACGAGGGTCGTTCCACGTTAGTCTGAGTAACGGAAGCTGTAGACAA

8B         D  A  N  L  C  A  P  S  K  V  Q  S  D  S  L  P  S  T  S  V  -

8A         GACAGCATAGAGACATGTCAAAGATTAGATCCTCTTCACCAAAGCCTTAATTTATCCGAA
     421   ---------+---------+---------+---------+---------+---------+ 480
           CTGTCGTATCTCTGTACAGTTTCTAATCTAGGAGAAGTGGTTTCGGAATTAAATAGGCTT

8B         D  S  I  E  T  C  Q  R  L  D  P  L  H  Q  S  L  N  L  S  E  -

8A         AGGACACCCAGAGTTATACTGACGGATATCCGGCAAACAGAATTAGGAAGAAAATATTTA
     481   ---------+---------+---------+---------+---------+---------+ 540
           TCCTGTGGGTCTCAATATGACTGCCTATAGGCCGTTTGTCTTAATCCTTCTTTTATAAAT

8B         R  T  P  R  V  I  L  T  D  I  R  Q  T  E  L  G  R  K  Y  L  -

8A         AAGATCCCACCTGTAACTGAGGCCAGTTTGAGTGATACAGCCAACCTGAAATCAGAGCAA
     541   ---------+---------+---------+---------+---------+---------+ 600
           TTCTAGGGTGGACATTGACTCCGGTCAAACTCACTATGTCGGTTGGACTTTAGTCTCGTT

8B         K  I  P  P  V  T  E  A  S  L  S  D  T  A  N  L  K  S  E  Q  -

8A         CTTTCTTCATCATCTGATGGCAGCTTAGAGTCTTGTCAGAGTGTAAATCATCACAAGAGC
     601   ---------+---------+---------+---------+---------+---------+ 660
           GAAAGAAGTAGTAGACTACCGTCGAATCTCAGAACAGTCTCACATTTAGTAGTGTTCTCG

8B         L  S  S  S  S  D  G  S  L  E  S  C  Q  S  V  N  H  H  K  S  -

8A         TTTTTATCTGAAAGTGGTCCCAAACCAAGTAGGACAGGTGACGTTCCTGCAAAGGAGGCT
     661   ---------+---------+---------+---------+---------+---------+ 720
           AAAAATAGACTTTCACCAGGGTTTGGTTCATCCTGTCCACTGCAAGGACGTTTCCTCCGA

8B         F  L  S  E  S  G  P  K  P  S  R  T  G  D  V  P  A  K  E  A  -

8A         GCATGTGGGGACAGAAGCAGGGTGATGATGGAGGAGTCACTCCTGAGATGGCTGCTCCT
     721   ---------+---------+---------+---------+---------+---------+ 780
           CGTACACCCCCTGTCTTCGTCCCACTACTACCTCCTCAGTGAGGACTCTACCGACGAGGA

```
8A        CATCCTAAAGGTTCGTGACTGCTAGAGACGAAGTCAGACTTATTGTATTTACAATGATTT
        781 ---------+---------+---------+---------+---------+---------+ 840
          GTAGGATTTCCAAGCACTGACGATCTCTGCTTCAGTCTGAATAACATAAATGTTACTAAA

8B         H  P  K  G  S  *

8A        TTATTATGAATGTTTCATATTAACATTGAAAGGATATATAAAAGTAAATGGGGGTAAATC
        841 ---------+---------+---------+---------+---------+---------+ 900
          AATAATACTTACAAAGTATAATTGTAACTTTCCTATATATTTTCATTTACCCCCATTTAG

8A        TCGAG
        901 ----- 905
          AGCTC
```

FIG. 8A and FIG. 8B cont.

```
9A      ggcctcgaggccaagaattcggcacgaggggtgacagcgcctgcaactgaaatttcagca
     1  ------------+---------+---------+---------+---------+---------+ 60
        ccggagctccggttcttaagccgtgctccccactgtcgcggacgttgactttaaagtcgt 9A      gcgggagaagatggacaagagaaagctcgggcgacggccatcttcatccgaaatcatcac
    61  ------------+---------+---------+---------+---------+---------+ 120
        cgccctcttctacctgttctctttcgagcccgctgccggtagaagtaggctttagtagtg

9B              M  D  K  R  K  L  G  R  R  P  S  S  S  E  I  I  T  -

9A      agaaggaaaaaggaaaaagtcatcttctgatttatcggagataagaaagatgttaaatgc
   121  ------------+---------+---------+---------+---------+---------+ 180
        tcttccttttccttttcagtagaagactaaatagcctctattctttctacaatttacg

9B           E  G  K  R  K  K  S  S  S  D  L  S  E  I  R  K  M  L  N  A  -

9A      aaaccagaggatgtccatgttcaatcaccactgtccaaattcagaagctcagaacgctg
   181  ------------+---------+---------+---------+---------+---------+ 240
        ttttggtctcctacaggtacaagttagtggtgacaggtttaagtcttcgagtcttgcgac

9B           K  P  E  D  V  H  V  Q  S  P  L  S  K  F  R  S  S  E  R  W  -

9A      gactctcccttgcagtgggaaagaagcctaaggaataaagtcatctctctagaccataa
   241  ------------+---------+---------+---------+---------+---------+ 300
        ctgagagggaaacgtcaccctttcttcggattccttatttcagtagagagatctggtatt

9B           T  L  P  L  Q  W  E  R  S  L  R  N  K  V  I  S  L  D  H  K  -

9A      aaataaaaaacatatccgagggtgtcctgttacttccaagtcatcaccagaaaggcaact
   301  ------------+---------+---------+---------+---------+---------+ 360
        tttatttttgtataggctcccacaggacaatgaaggttcagtagtggtcttccgttga

```
9A        caaagttatgttgacgaatgtcctatggacggatttaggacgaaaattcagaaagaccct
    361   ------------+---------+---------+---------+---------+---------+ 420
          gtttcaatacaactgcttacaggatacctgcctaaatcctgcttttaagtctttctggga

9B          K  V  M  L  T  N  V  L  W  T  D  L  G  R  K  F  R  K  T  L  -

9A        acctagaaacgatgctaatttatgtgatgccaacaaggtgcaatcagactcattgccttc
    421   ------------+---------+---------+---------+---------+---------+ 480
          tggatctttgctacgattaaatacactacggttgttccacgttagtctgagtaacggaag

9B          P  R  N  D  A  N  L  C  D  A  N  K  V  Q  S  D  S  L  P  S  -

9A        gacatctgttgacagcctagagacatgtcaaagattagaacctcttcgccaaagccttaa
    481   ------------+---------+---------+---------+---------+---------+ 540
          ctgtagacaactgtcggatctctgtacagtttctaatcttggagaagcggtttcggaatt

9B          T  S  V  D  S  L  E  T  C  Q  R  L  E  P  L  R  Q  S  L  N  -

9A        tttatctgaaaggatacccagagttatattgacgaatgtcctgggaacggagttaggaag
    541   ------------+---------+---------+---------+---------+---------+ 600
          aaatagactttcctatgggtctcaatataactgcttacaggacccttgcctcaatcctcc

9B          L  S  E  R  I  P  R  V  I  L  T  N  V  L  G  T  E  L  G  R  -

9A        aaaatacataaggaccccacctgtaactgagggaagtttgagtgatacagacaacttgca
    601   ------------+---------+---------+---------+---------+---------+ 660
          ttttatgtattcctggggtggacattgactcccttcaaactcactatgtctgttgaacgt

9B          K  Y  I  R  T  P  P  V  T  E  G  S  L  S  D  T  D  N  L  Q  -

9A        atcagagcaactttcttcatcatctgatggcagcctagaatcttatcaaaatctaaaccc
    661   ------------+---------+---------+---------+---------+---------+ 720
          tagtctcgttgaaagaagtagtagactaccgtcggatcttagaatagttttagatttggg

```
9A           tcacaagagctgttatttatctgaaagggggctcacaacgaagtaagacagtagatgacaa
       721   ---------+---------+---------+---------+---------+---------+  780
             agtgttctcgacaataaatagactttcccccgagtgttgcttcattctgtcatctactgtt

9B            H  K  S  C  Y  L  S  E  R  G  S  Q  R  S  K  T  V  D  D  N  -

9A           ttctgcaaagcagactgcgcacaataaagaaaaacgaagaaaggatgatggcatttctct
       781   ---------+---------+---------+---------+---------+---------+  840
             aagacgtttcgtctgacgcgtgttatttcttttttgcttctttcctactaccgtaaagaga

9B            S  A  K  Q  T  A  H  N  K  E  K  R  R  K  D  D  G  I  S  L  -

9A           tttaatatctgatactcagcctgaaggtttgtgaaccttagaaaactgttggaatttgaa
       841   ---------+---------+---------+---------+---------+---------+  900
             aaattatagactatgagtcggacttccaaacacttggaatcttttgacaaccttaaactt

9B            L  I  S  D  T  Q  P  E  G  L  *

9A           ttttttcttattgtattaataataattttttgttataaataaattatttttatttttacttttg
       901   ---------+---------+---------+---------+---------+---------+  960
             aaaaaagaataacataattattattaaaaacaatatttatttaataaaataaaatgaaac 9A           aaaggatatgtgaaagtaaagggagattatttggcaacacaaataaaactgttggaattt
       961   ---------+---------+---------+---------+---------+---------+ 1020
             tttcctatacactttcatttccctctaataaaccgttgtgtttattttgacaaccttaaa 9A           gaattttttcttattgtattaataataattttttgttataaataaattatttttatttttact
      1021   ---------+---------+---------+---------+---------+---------+ 1080
             cttaaaaaagaataacataattattattaaaaacaatatttatttaataaaataaaatga 9A           ttgaaaggatatgtgaaagtaaagggagattatttggcaacacaaataaaattgctaaac
      1081   ---------+---------+---------+---------+---------+---------+ 1140
             aactttcctatacactttcatttccctctaataaaccgttgtgtttattttaacgatttg 9A           ctcaaaaaaaaaaaaaaaaaaaaaaaaaattggcggccgcaagcttagctt
      1141   ---------+---------+---------+---------+--------- 1189
             gagttttttttttttttttttttttttttaaccgccggcgttcgaatcgaa
```

FIG. 9A and FIG. 9B cont.

Comparison of murine and human nucleotide sequences of MHRII-AP62

```
m    :  198 aagaagcctaagaaataaagtcatctgtctagaccacaaaaaaccaaaagctgcccgtgg 257
             ||||||||||||| ||||||||||||| ||||||||| |||||   ||||  |  ||| ||
hu   :  262 aagaagcctaaggaataaagtcatctctctagaccataaaaataaaaaacatatccgagg 321 m    :  258 gtgtcctccta------agggattaccaaaaaggcatctcagagttatgttgacgaatgt 311
             |||||||  ||          ||   ||  |||| ||||||| ||||||||||||||||||
hu   :  322 gtgtcctgttacttccaagtcatcaccagaaaggcaactcaaagttatgttgacgaatgt 381 m    :  312 tctatggacggacttaggacgagaattcagaaagaccctgcctagaaaggatgctaattt 371
             |||||||||||| ||||||||||  |||||||||||||| ||||||||| ||||||||||
hu   :  382 cctatggacggatttaggacgaaaattcagaaagaccctacctagaaacgatgctaattt 441 m    :  372 atgtgctcccagcaaggtgcaatcagactcattgccttcgacatctgttgacagcataga 431
             ||||| | ||| ||||||||||||||||||||||||||||||||||||||||||||  ||||
hu   :  442 atgtgatgccaacaaggtgcaatcagactcattgccttcgacatctgttgacagcctaga 501 m    :  432 gacatgtcaaagattagatcctcttcaccaaagccttaatttatccgaaaggacacccag 491
             ||||||||||||||||||| |||||||  |||||||||||||||| ||||||| ||||||
hu   :  502 gacatgtcaaagattagaacctcttcgccaaagccttaatttatctgaaaggatacccag 561 m    :  492 agttatactgacggatatccggcaaacagaattaggaagaaaatatttaaagatcccacc 551
             ||||||| |||||  || |||  |||  || |||||||||||||||  || || |||||||
hu   :  562 agttatattgacgaatgtcctgggaacggagttaggaagaaaatacataaggacccccacc 621 m    :  552 tgtaactgaggccagtttgagtgatacagccaacctgaaatcagagcaactttcttcatc 611
             |||||||||||  |||||||||||||||||| |||| || ||||||||||||||||||||||
hu   :  622 tgtaactgagggaagtttgagtgatacagacaacttgcaatcagagcaactttcttcatc 681 m    :  612 atctgatggcagcttagagtcttgtcagagtgtaaatcatcacaagagc---tttttatc 668
             |||||||||||||| ||||  |||| |||  || | | |||| | |||||||||    | ||||||
hu   :  682 atctgatggcagcctagaatcttatcaaaatctaaaccctcacaagagctgttatttatc 741 m    :  669 tgaaagtggtcccaaaccaagtaggacag 697
             ||||||  ||   |||  |||||  |||||
hu   :  742 tgaaaggggctcacaacgaagtaagacag 770
```

FIG. 10

Comparison of Mouse and Human MHRII-AP62 proteins

```
m  :   1 MDRARPGRRRASSEIVTEGKQKRSSPPHLQKITKLLTVKSEDVLAQSPLSKLRGSECW--  58
         MD+ + GRR +SSEI+TEGK+K+SS   L +I K+L  K EDV  QSPLSK R SE W
hu :   1 MDKRKLGRRPSSSEIITEGKRKKSSSD-LSEIRKMLNAKPEDVHVQSPLSKFRSSERWTL 59 m  :  59 ---WTRSLRNKVICLDHKKPKAARGCP--PKGLPKRHLRVMLTNVLWTDLGREFRKTLPR 113
            W RSLRNKVI LDHK K  RGCP   K P+R L+VMLTNVLWTDLGR+FRKTLPR
hu :  60 PLQWERSLRNKVISLDHKNKKHIRGCPVTSKSSPERQLKVMLTNVLWTDLGRKFRKTLPR 119 m  : 114 KDANLCAPSKVQSDSLPSTSVDSIETCQRLDPLHQSLNLSERTPRVILTDIRQTELGRKY 173
          DANLC  +KVQSDSLPSTSVDS+ETCQRL+PL QSLNLSER PRVILT++  TELGRKY
hu : 120 NDANLCDANKVQSDSLPSTSVDSLETCQRLEPLRQSLNLSERIPRVILTNVLGTELGRKY 179 m  : 174 LKIPPVTEASLSDTANLKXXXXXXXXXXXXXXXXXXXVNHHKS-FLSESGPKPSRT-GDVPA 231
         ++ PPVTE SLSDT NL+                   +N HKS +LSE G + S+T  D  A
hu : 180 IRTPPVTEGSLSDTDNLQSEQLSSSSDGSLESYQNLNPHKSCYLSERGSQRSKTVDDNSA 239 m  : 232 KEAACGGQKQGDDGGVTPEMAAPHPKG 258
         K+  A   +K+ D G++   ++   P+G
hu : 240 KQTAHNKEKRRKDDGISLLISDTQPEG 266
```

FIG. 11

SEQUENCE LISTING

```
<160> NUMBER OF SEQ ID NOS: 9

<210> SEQ ID NO 1
<211> LENGTH: 24
<212> TYPE: DNA
<213> ORGANISM: MOUSE

<400> SEQUENCE: 1
tgatgaccga attccttgga ggag                                          24

<210> SEQ ID NO 2
<211> LENGTH: 20
<212> TYPE: DNA
<213> ORGANISM: MOUSE

<400> SEQUENCE: 2
ccagcttggc agcggctgag                                               20

<210> SEQ ID NO 3
<211> LENGTH: 334
<212> TYPE: DNA
<213> ORGANISM: MOUSE

<400> SEQUENCE: 3
cctcgagagt tcacatcaga gattgttaca gagggaaaac agaagaggtc atcaccacct    60
catttacaga agataacaaa gttgttaact gtaaagtcag aggatgttct tgctcagtca   120
ccattgtcca aactcagagg ctcagaatgc tggtggacaa gaagcctaag aaataaagtc   180
atctgtctag accacaaaaa accaaaagct gcccgtgggt gtcctcctaa gggattacca   240
aaaaggcatc tcagagttat gttgacgaat gttctatgga cggacttagg acgagaattc   300
agaaagaccc tgcctagaaa ggatgctaat ttat                              334

<210> SEQ ID NO 4
<211> LENGTH: 111
<212> TYPE: PRT
<213> ORGANISM: MOUSE

<400> SEQUENCE: 4

Pro Arg Glu Phe Thr Ser Glu Ile Val Thr Glu Gly Lys Gln Lys Arg
1               5                   10                  15

Ser Ser Pro Pro His Leu Gln Lys Ile Thr Leu Leu Thr Val Lys Ser
            20                  25                  30

Glu Asp Val Leu Ala Gln Ser Pro Leu Ser Lys Leu Arg Gly Ser Glu
        35                  40                  45
```

```
Cys Trp Trp Thr Arg Ser Leu Arg Asn Lys Val Ile Cys Leu Asp His
    50                  55                  60

Lys Lys Pro Lys Ala Ala Arg Gly Cys Pro Pro Lys Gly Leu Pro Lys
65                  70                  75                  80

Arg His Leu Leu Arg Val Met Leu Thr Asn Val Leu Trp Thr Asp Leu
                    85                  90                  95

Gly Arg Glu Phe Arg Lys Thr Leu Pro Arg Lys Asp Ala Asn Leu
                100                 105                 110
```

<210> SEQ ID NO 5
<211> LENGTH: 905
<212> TYPE: DNA
<213> ORGANISM: MOUSE

<400> SEQUENCE: 5

```
cgcccgggca ggtagaagat ggacagggcc aggcctgggc gtcggcgacg ttcatcagag      60
attgttacag agggaaaaca gaagaggtca tcaccacctc atttacagaa gataacaaag    120
ttgttaactg taaagtcaga ggatgttctt gctcagtcac cattgtccaa actcagaggc    180
tcagaatgct ggtggacaag aagcctaaga aataaagtca tctgtctaga ccacaaaaaa    240
ccaaaagctg cccgtgggtg tcctcctaag ggattaccaa aaaggcatct cagagttatg    300
ttgacgaatg ttctatggac ggacttagga cgagaattca gaaagaccct gcctagaaag    360
gatgctaatt tatgtgctcc cagcaaggtg caatcagact cattgccttc gacatctgtt    420
gacagcatag agacatgtca agattagat cctcttcacc aaagccttaa tttatccgaa     480
aggacaccca gagttatact gacggatatc cggcaaacag aattaggaag aaaatattta    540
aagatcccac ctgtaactga ggccagtttg agtgatacag ccaacctgaa atcagagcaa    600
ctttcttcat catctgatgg cagcttagag tcttgtcaga gtgtaaatca tcacaagagc    660
tttttatctg aaagtggtcc caaaccaagt aggacaggtg acgttcctgc aaaggaggct    720
gcatgtgggg gacagaagca gggtgatgat ggaggagtca ctcctgagat ggctgctcct    780
catcctaaag gttcgtgact gctagagacg aagtcagact tattgtattt acaatgattt    840
ttattatgaa tgtttcatat taacattgaa aggatatata aaagtaaatg ggggtaaatc    900
tcgag                                                                905
```

<210> SEQ ID NO 6
<211> LENGTH: 199
<212> TYPE: PRT
<213> ORGANISM: MOUSE

<400> SEQUENCE: 6

```
Met Asp Arg Ala Arg Pro Gly Arg Arg Ala Ser Ser Glu Ile Val
1               5                   10                  15

Thr Glu Gly Lys Gln Lys Arg Ser Ser Pro His Leu Gln Lys Ile
                20                  25                  30

Thr Lys Leu Leu Thr Val Lys Ser Glu Asp Val Leu Ala Gln Ser Pro
                35                  40                  45

Leu Ser Lys Leu Arg Gly Pro Lys Ala Ala Arg Gly Cys Pro Pro Lys
    50                  55                  60

Gly Leu Pro Lys Arg His Leu Arg Val Met Asp Ala Asn Leu Cys Ala
65                  70                  75                  80

Pro Ser Lys Val Gln Ser Asp Ser Leu Pro Ser Thr Ser Val Asp Ser
                85                  90                  95
```

```
Ile Glu Thr Cys Gln Arg Leu Asp Pro Leu His Gln Ser Leu Asn Leu
            100                 105                 110

Ser Glu Arg Thr Pro Arg Val Ile Leu Thr Asp Ile Arg Gln Thr Glu
            115                 120                 125

Leu Gly Arg Lys Tyr Leu Leu Ser Ser Ser Ser Asp Gly Ser Leu Glu
            130                 135                 140

Ser Cys Gln Ser Val Asn His His Lys Ser Phe Leu Ser Glu Ser Gly
145                 150                 155                 160

Pro Lys Pro Ser Arg Thr Gly Asp Val Pro Ala Lys Glu Ala Ala Cys
                165                 170                 175

Gly Gly Gln Lys Gln Gly Asp Asp Gly Gly Val Thr Pro Glu Met Ala
            180                 185                 190

Ala Pro His Pro Lys Gly Ser
            195

<210> SEQ ID NO 7
<211> LENGTH: 1189
<212> TYPE: DNA
<213> ORGANISM: HUMAN

<400> SEQUENCE: 7
ggcctcgagg ccaagaattc ggcacgaggg gtgacagcgc ctgcaactga aatttcagca      60
gcgggagaag atggacaaga gaaagctcgg gcgacggcca tcttcatccg aaatcatcac     120
agaaggaaaa aggaaaaagt catcttctga tttatcggag ataagaaaga tgttaaatgc     180
aaaaccagag gatgtccatg ttcaatcacc actgtccaaa ttcagaagct cagaacgctg     240
gactctccct ttgcagtggg aaagaagcct aaggaataaa gtcatctctc tagaccataa     300
aaataaaaaa catatccgag ggtgtcctgt tacttccaag tcatcaccag aaaggcaact     360
caaagttatg ttgacgaatg tcctatggac ggatttagga cgaaaattca gaaagaccct     420
acctagaaac gatgctaatt tatgtgatgc caacaaggtg caatcagact cattgccttc     480
gacatctgtt gacagcctag agacatgtca aagattagaa cctcttcgcc aaagccttaa     540
tttatctgaa aggataccca gagttatatt gacgaatgtc ctgggaacgg agttaggaag     600
aaaatacata aggaccccac ctgtaactga gggaagtttg agtgatacag acaacttgca     660
atcagagcaa ctttcttcat catctgatgg cagcctagat tcttatcaaa atctaaaccc     720
tcacaagagc tgtttatttat ctgaaagggg ctcacaacga agtaagacag tagatgacaa     780
ttctgcaaag cagactgcgc acaataaaga aaaacgaaga aaggatgatg gcatttctct     840
tttaatatct gatactcagc ctgaaggttt gtgaacctta gaaaactgtt ggaatttgaa     900 tttttttctta ttgtattaat aataatttttt gttataaata aattatttta ttttactttg     960
aaaggatatg tgaaagtaaa gggagattat ttggcaacac aaataaaact gttggaattt    1020
gaattttttc ttattgtatt aataataatt tttgttataa ataaattatt ttatttttact    1080 ttgaaaggat atgtgaaagt aaagggagat tatttggcaa cacaaataaa attgctaaac    1140
ctcaaaaaaa aaaaaaaaaa aaaaaaattg gcggccgcaa gcttagctt                1189

<210> SEQ ID NO 8
<211> LENGTH: 198
<212> TYPE: PRT
<213> ORGANISM: HUMAN

<400> SEQUENCE: 8

Lys Val Ile Ser Leu Asp His Lys Asn Lys Lys His Ile Arg Gly Cys
                  5                  10                  15
```

-continued

```
Pro Val Thr Ser Lys Ser Ser Pro Glu Arg Gln Leu Lys Val Met Leu
                20                  25                  30

Thr Asn Val Leu Trp Thr Asp Leu Gly Arg Lys Phe Arg Lys Thr Leu
            35                  40                  45

Pro Arg Asn Asp Ala Asn Leu Cys Asp Ala Asn Lys Val Gln Ser Asp
 50                  55                  60

Ser Leu Pro Ser Thr Ser Val Asp Ser Leu Glu Thr Cys Gln Arg Leu
 65                  70                  75                  80

Glu Pro Leu Arg Gln Ser Leu Asn Leu Ser Glu Arg Ile Pro Arg Val
                85                  90                  95

Ile Leu Thr Asn Val Leu Gly Thr Glu Leu Gly Arg Lys Tyr Ile Arg
            100                 105                 110

Thr Pro Pro Val Thr Glu Gly Ser Leu Ser Asp Thr Asp Asn Leu Gln
            115                 120                 125

Ser Glu Gln Leu Ser Ser Ser Asp Gly Ser Leu Glu Ser Tyr Gln
        130                 135                 140

Asn Leu Asn Pro His Lys Ser Cys Tyr Leu Ser Glu Arg Gly Ser Gln
145                 150                 155                 160

Arg Ser Lys Thr Val Asp Asp Asn Ser Ala Lys Gln Thr Ala His Asn
                165                 170                 175

Lys Glu Lys Arg Arg Lys Asp Asp Gly Ile Ser Leu Leu Ile Ser Asp
            180                 185                 190

Thr Gln Pro Glu Gly Leu
        195
```

<210> SEQ ID NO 9
<211> LENGTH: 258
<212> TYPE: PRT
<213> ORGANISM: MOUSE
<220> FEATURE:
<221> NAME/KEY: variant
<222> LOCATION: amino acid residues 192-218
<223> OTHER INFORMATION: Xaa may be any of the 20 amino acids which occur naturally in mammals.

<400> SEQUENCE: 9

```
Met Asp Arg Ala Arg Pro Gly Arg Arg Ala Ser Ser Glu Ile Val
1               5                   10                  15

Thr Glu Gly Lys Gln Lys Arg Ser Ser Pro Pro His Leu Gln Lys Ile
                20                  25                  30

Thr Lys Leu Leu Thr Val Lys Ser Glu Asp Val Leu Ala Gln Ser Pro
            35                  40                  45

Leu Ser Lys Leu Arg Gly Ser Glu Cys Trp Trp Thr Arg Ser Leu Arg
 50                  55                  60

Asn Lys Val Ile Cys Leu Asp His Lys Lys Pro Lys Ala Ala Arg Gly
 65                  70                  75                  80

Cys Pro Pro Lys Gly Leu Pro Lys Arg His Leu Arg Val Met Leu Thr
                85                  90                  95

Asn Val Leu Trp Thr Asp Leu Gly Arg Glu Phe Arg Lys Thr Leu Pro
            100                 105                 110

Arg Lys Asp Ala Asn Leu Cys Ala Pro Ser Lys Val Gln Ser Asp Ser
            115                 120                 125

Leu Pro Ser Thr Ser Val Asp Ser Ile Glu Thr Cys Gln Arg Leu Asp
        130                 135                 140

Pro Leu His Gln Ser Leu Asn Leu Ser Glu Arg Thr Pro Arg Val Ile
145                 150                 155                 160
```

-continued

```
Leu Thr Asp Ile Arg Gln Thr Glu Leu Gly Arg Lys Tyr Leu Lys Ile
            165                 170                 175

Pro Pro Val Thr Glu Ala Ser Leu Ser Asp Thr Ala Asn Leu Lys Xaa
            180                 185                 190

Xaa Xaa Xaa Xaa Xaa Xaa Xaa Xaa Xaa Xaa Xaa Xaa Xaa Xaa Xaa Xaa
            195                 200                 205

Val Asn His His Lys Ser Phe Leu Ser Glu Ser Gly Pro Lys Pro Ser
    210                 215                 220

Arg Thr Gly Asp Val Pro Ala Lys Glu Ala Ala Cys Gly Gly Gln Lys
225                 230                 235                 240

Gln Gly Asp Asp Gly Gly Val Thr Pro Glu Met Ala Ala Pro His Pro
            245                 250                 255

Lys Gly
```

MYC HOMOLOGY REGION II—ASSOCIATED PROTEIN AND USES THEREOF

RELATED APPLICATION

This application is a continuation-in-part of U.S. application Ser. No. 08/946,692, filed Oct. 8, 1997, U.S. Pat. No. 6,040,425, the contents of which are expressly incorporated herein by reference.

STATEMENT OF GOVERNMENT INTEREST

This invention was made with government support under NIH Grant No. RO1 HD28317. As such, the government has certain rights in this invention.

BACKGROUND OF THE INVENTION

Members of the Myc family of nuclear protooncogenes (c-, N- and L-Myc) play central roles in the control of normal growth and development and in genetic pathways linked to cellular transformation and apoptotic cell death. Accumulating structural, biochemical and genetic evidence affords the view that the function of Myc family oncoproteins in these diverse processes relates in part to their roles as sequence-specific transcription factors. Myc family proteins possess a multifunctional amino-terminal domain with transactivation potential, a region rich in basic amino acid residues responsible for sequence-specific DNA-binding activity, and a carboxy-terminal alpha-helical domain required for dimerization with another bHLH/LZ protein, Max. All known biological and biochemical activities of Myc are highly dependent upon its association with Max. In addition to its key role as an obligate partner in transactivation-competent Myc/Max complexes, Max can also repress Myc-responsive genes through the formation of transcriptional-repression complexes with members of the Mad family.

Several lines of evidence support the view that Mad and Mxi1 are important tumor suppressors. First, the addition of Mad or Mxi1 can dramatically reduce the oncogenic activity of Myc/Ras in the REF cooperation assay. Second, Nisen and coworkers (Chen, J., Willingham, T., Margraf, L. R., Schreiber-Agus, N., DePinho, R. A., and Nisen, P. D., *Nature Medicine* 1:638–643 (1995)) have shown that adenoviral constructs encoding Mad profoundly inhibit the proliferation and tumorigenicity of established human tumor cell lines. Third, Mad and Mxi1 map to cancer hotspots that are altered in a broad spectrum of different tumor types. Lastly, the preliminary assessment of Mxi1 knockout mice indicates that Mxi1-deficiency is associated with a cancer-prone condition.

From a mechanistic standpoint, the ability of Mad and Mxi1 to act as potent anti-Myc agents is dependent upon a short amino-terminal alpha-helical domain that allows for association with a mammalian protein that is structurally homologous to the yeast transcriptional repressor SIN3. The mechanistic basis for the mouse Sin3-mediated repression appears to be mediated in part through the recruitment of: (1) NcoR, a nuclear co-repressor that directly impacts on Pol II activity and (2) HD-1, a histone deacetylase that deacetylates histone H3 and H4 tails resulting in a condensed and less accessible nucleosomal arrangement. Structure-function studies of Sin3 indicate that its interaction with HD-1 is a critical requirement for Sin3-mediated anti-oncogenic activity in the context of Myc-induced cellular transformation.

Two domains known to be absolutely essential for Myc oncogenic activity have been mapped to the C-terminal bHLH/LZ structure and an amino-terminal segment designated Myc homology region II (MHRII). The inventors have recently cloned the drosophila homologue of Myc and have demonstrated that both of these signature features are conserved and, more strikingly, that drosophila Myc gene is oncogenic in mammalian cells. Over-expression of an MHRII fragment has been shown by others to inhibit the ability of Myc or E1a to cooperate with activated Ras in the REF assay. This finding, coupled with the formation of a specific complex between MHRII and a nuclear factor, suggests that MHRII oncogenic activity is dependent upon its ability to interact with an unidentified nuclear factor.

Myc has been shown to be directly involved in the genesis and progression of many different tumor types. Moreover, even when Myc deregulation is not the principal genetic lesion in human cancers, many cancer-associated lesions affect signaling pathways that feed into Myc and require Myc function in order to maintain the malignant phenotype.

Accordingly, there is a great need for the discovery of and characterization of proteins that interact with the MHRII of Myc. The isolation and characterization of proteins that interact with the MHRII of Myc allows for the design of agents that interact directly with MHRII to affect the regulation of Myc and ultimately target the actions of Myc. Targeting the actions of Myc oncoprotein can potentially have a significant impact on a very wide variety of human cancers, as well as many disorders arising from deregulated cellular growth or survival such as auto-immune disorders and psoriasis, among others.

SUMMARY OF THE INVENTION

The present invention provides for a novel purified Myc homology region II (MHRII) -associated protein, designated MHRII-AP62. Further provided by the present invention are antibodies immunoreactive with the MHRII-AP62 protein. Also provided are kits comprising MHRII-AP62 antibodies and methods of using the antibodies for the detection of the MHRII-AP62 protein and the diagnosis of cancers.

Further provided by the present invention is a nucleic acid sequence encoding the MHRII-AP62 protein, nucleic acid probes which hybridize to the nucleic acid sequence, and kits containing the probes for use in the diagnosis of cancers.

The present invention also provides a vector comprising a nucleic acid encoding a MHRII-AP62 protein, a cell stably transformed with this vector, as well as a method for producing recombinant MHRII-AP62 protein.

Also provided by the present invention are agents that mimic the activity of the MHRII-AP62 protein and bind to the binding domain of MHRII. Further provided are agents that inhibit the activity or expression of the MHRII-AP62 protein and inhibit the binding of the protein to MHRII, thus providing a means for assessing small molecule inhibitors to block or enhance MHRII-AP62 and MHRII interactions. Also provided are methods of treating cancer causing disease and reducing tumor growth using the agents.

Additional objects of the invention will be apparent from the description which follows.

BRIEF DESCRIPTION OF THE DRAWINGS

FIGS. 7A and 7B set forth the partial cDNA nucleic acid sequence (SEQ ID NO:3) (FIG. 7A), and the corresponding amino acid sequence (SEQ ID NO:4) (FIG. 7B), of the murine MHRII-AP62 protein.

FIGS. 8A and 8B set forth the complete cDNA nucleic acid sequence (SEQ ID NO:5) (FIG. 8A), and the corresponding amino acid sequence (SEQ ID NO:6) (FIG. 8B), of the murine MHRII-AP62 protein.

FIGS. 9A and 9B set forth the complete cDNA nucleic acid sequence (SEQ ID NO:7) (FIG. 9A), and the corresponding amino acid sequence (SEQ ID NO:8) (FIG. 9B), of the human MHRII-AP62 protein. The human cDNA was isolated by sequence comparison with the murine MHRII-AP62 cDNA of FIG. 8A. One of the aligned ESTs (Genebank Accession No. AI798977) was sequenced completely to obtain the sequence of FIG. 9A.

FIG. 10 is a comparison of the murine (bases 198–1697 of SEQ ID NO:5) and human (bases 262–770 of SEQ ID NO:7) MHRII-AP62 nucleotide sequences.

FIG. 11 is a comparison of the murine (SEQ ID NO:9) and human (amino acid residues 1–266 of SEQ ID NO:8) MHRII-AP62 amino acid sequences.

DETAILED DESCRIPTION OF THE INVENTION

Figure 1:
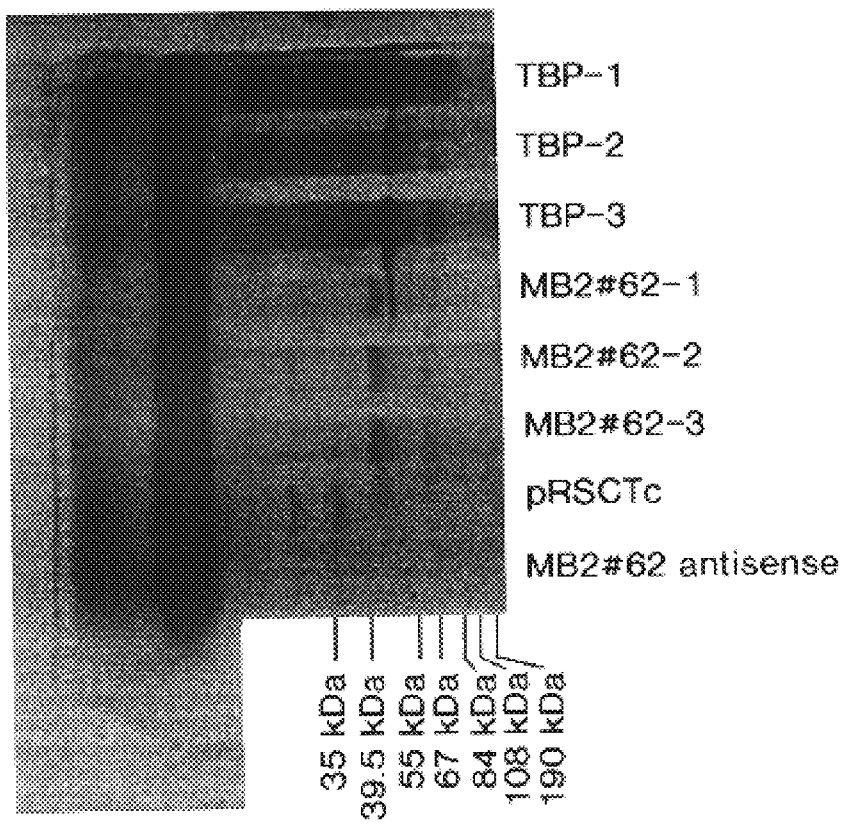
FIG. 1 sets forth results of in vitro transcription/translation experiments of MHRII-AP62 (TNT, Promega). The entire two hybrid derived cDNA produces a protein of ~45 kDa. The anti-sense construct (MHRII #62 antisense) and the empty vector (pRSCT c) were included as negative controls, while TBP (top three lanes) served as a positive control. MHRII #62 (lanes 4, 5 and 6 from the top) are from separate batches of the same reaction parameters. Molecular mass markers are shown in kilodaltons. The kDa marker sizes are as follows, starting from the top: 190, 108, 84, 67, 55, 39.5 and 35 kDa.
Figure 2:
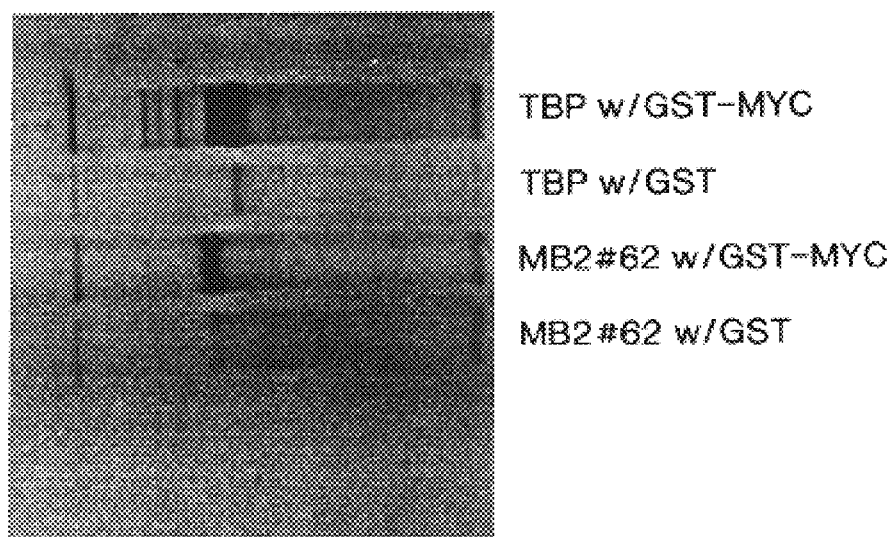
FIG. 2 sets forth the results of a GST pull down assay using the $^{35}$S, IVT product of AP62 with GST alone and GST-MYC (a.a.1-204). TBP w/GST was used as a positive control.
Figure 3A:
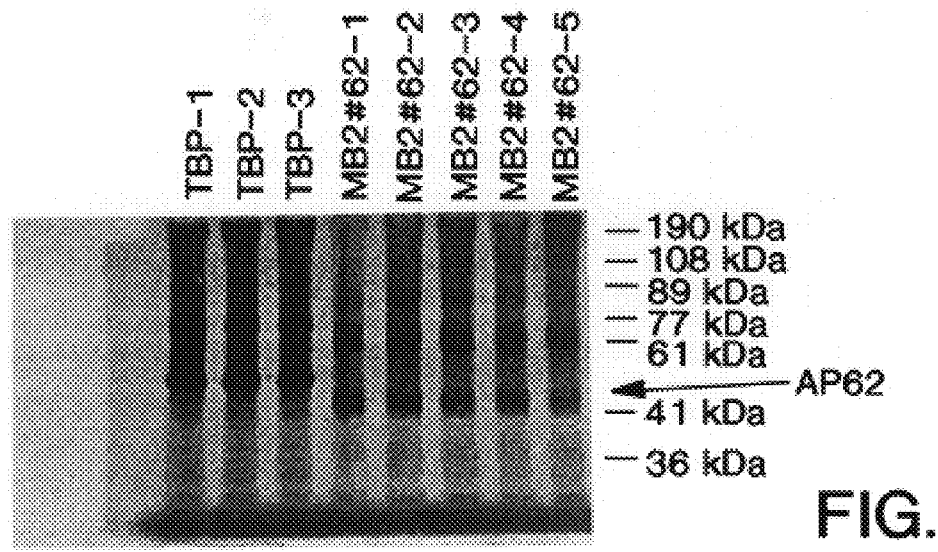
FIGS. 3A and 3B set forth the results of a GST pull down assay using the $^{35}$S, IVT product of MHRII-AP62 with GST alone, GST-MYC (a.a.1-204), GST-12S E1A or GST-13S E1A. TDP was used as a positive control.
Figure 3B:
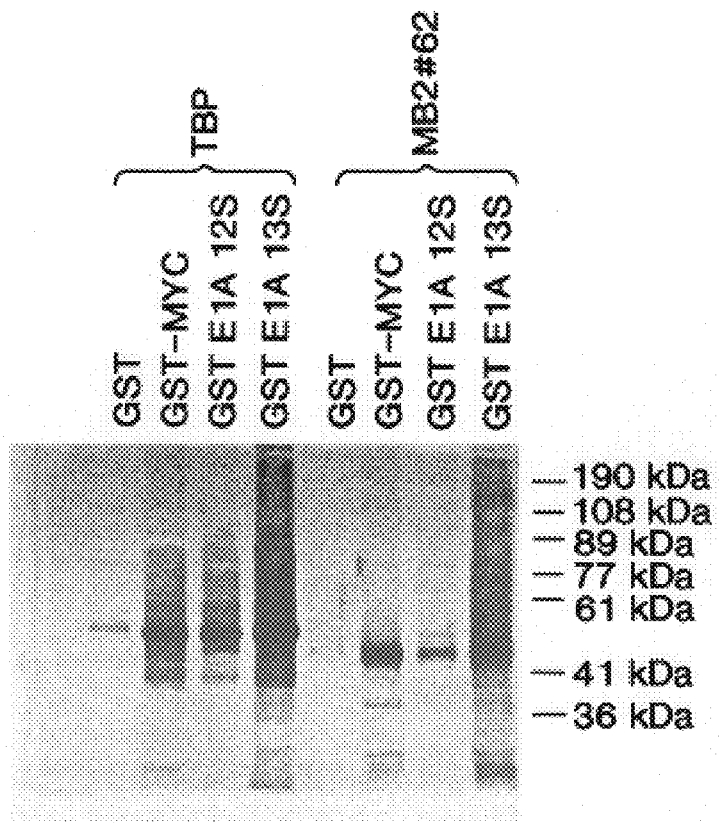
Figure 4A:
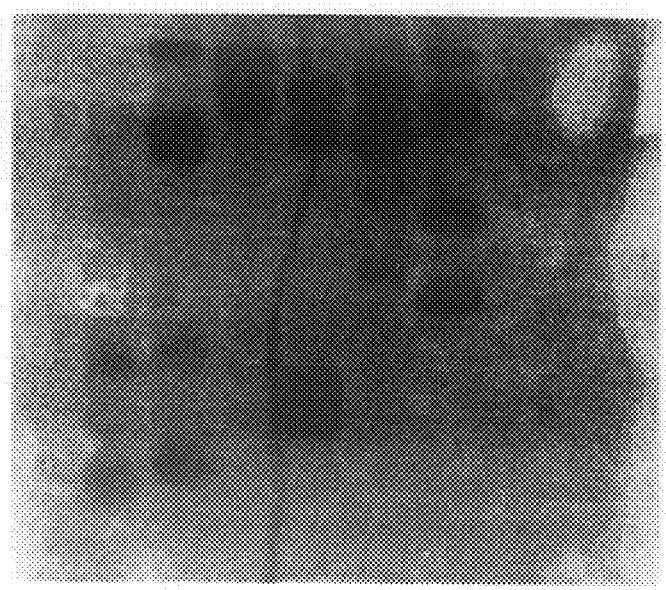
FIG. 4 sets forth the results of a zoo blot. Human, mouse, xenopus and zebra fish DNAs were probed with the entire two-hybrid derived fragment of MHRII-AP62.
Figure 4B:
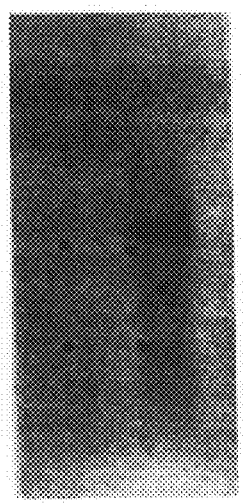
Figure 5:
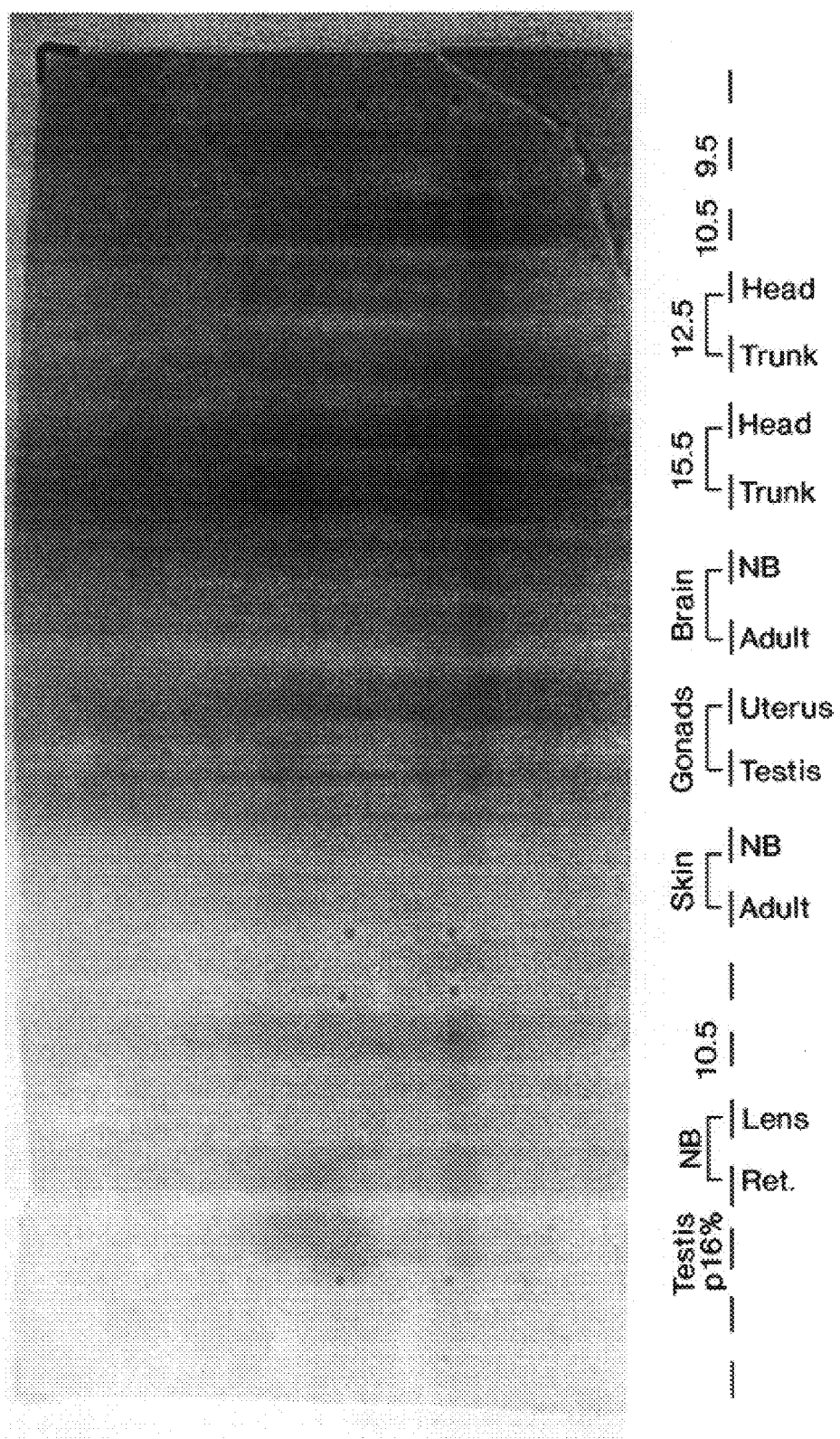
FIG. 5 sets forth the results of a Northern blot using MHRII-AP62 as a probe and mouse RNAs from different embryonic developmental stages and from different tissues in adults and newborns. The single ~5.2 kb transcript is seen, and appears to be up-regulated steadily from stages 9.5 to 15.5.
Figure 6:
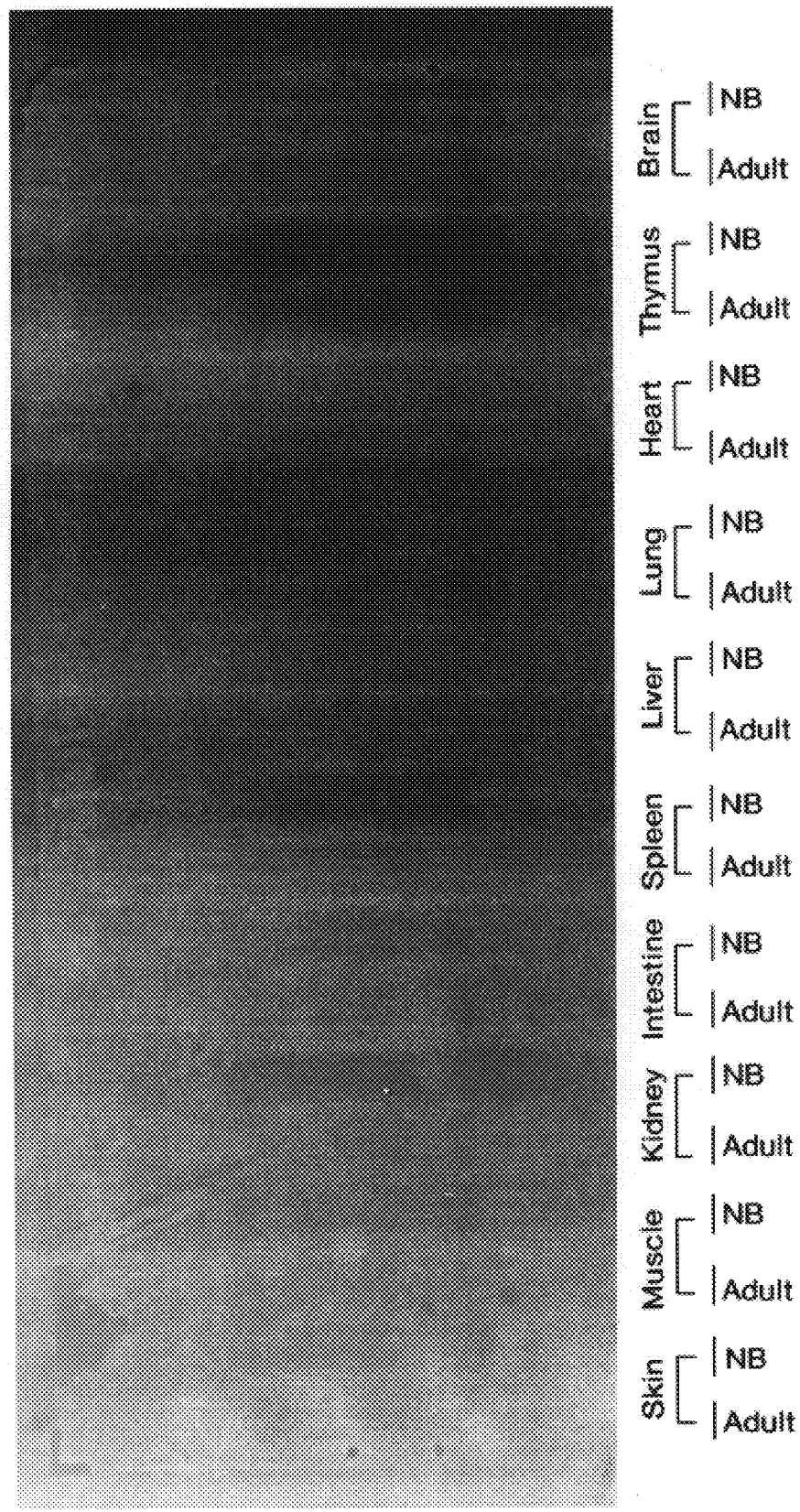
FIG. 6 shows the results of a Northern blot using MHRII-AP62 as a probe and mouse RNAs from different tissues of adult and newborn. The highest levels of expression are seen in thymus and spleen. Expression in brain and kidney correlates with Myc.
Figure 12:
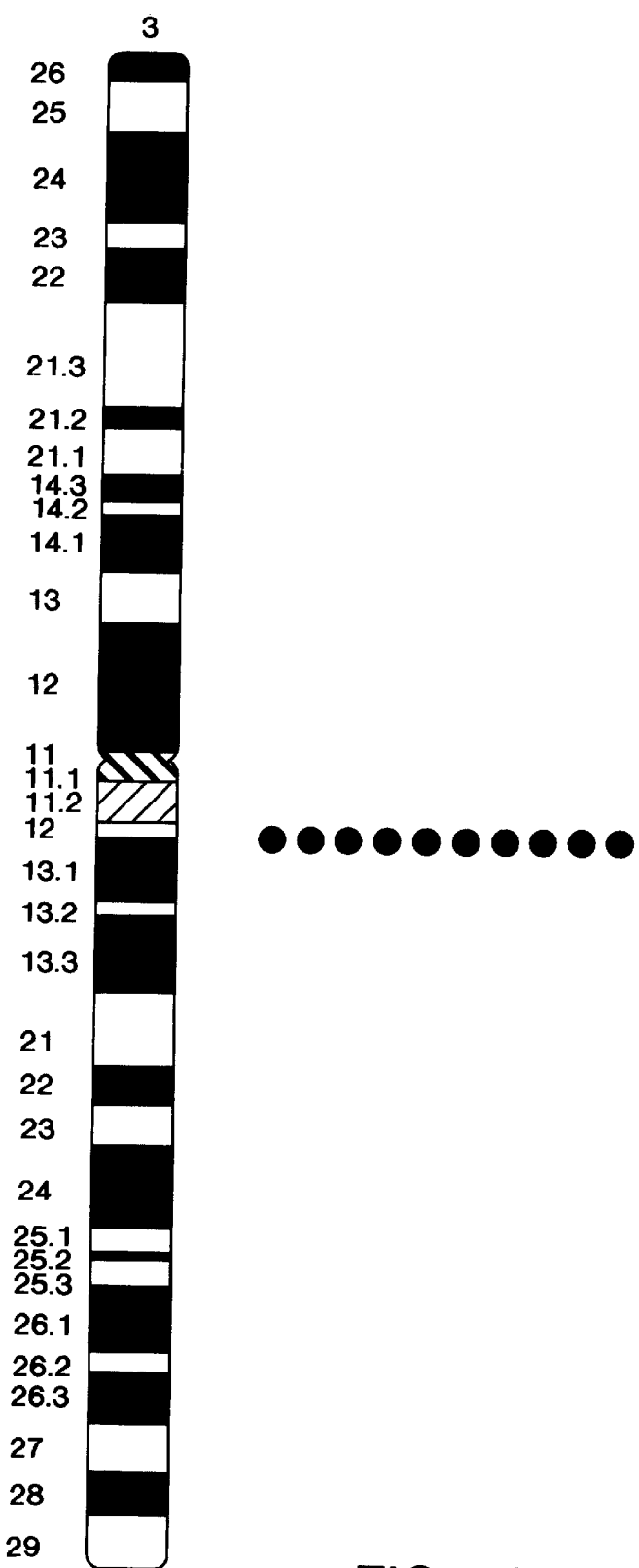
FIG. 12 indicates the localization of the MHRII-AP62 gene on the human chromosome, 3q12–q13.1.

The present invention provides for a novel purified Myc homology region II (MHRII)—associated protein, herein designated MHRII-AP62. As used herein, a "Myc homology region II—associated protein" is a protein that interacts with Myc homology region II to affect the oncogenic activity of MHRII. The MHRII-associated protein is preferably 40–50 kDa, and includes the human, rat and mouse analogues of the protein. Also provided by the present invention are mutated forms of the MHRII-AP62 protein. As used herein, a "mutated MHRII-AP62 protein" is the mutated form of the MHRII-AP62 protein, wherein the nucleic acid encoding the mutated MHRII-AP62 protein contains one or more deletion, insertion, point or rearrangement mutations, or a combination thereof, that may render the protein encoded by the nucleic acid nonfunctional or inactivated. The MHRII-AP62 protein of the present invention may be produced synthetically or recombinantly, or may be isolated from native cells.

The present invention also provides antibodies immunoreactive with the MHRII-AP62 protein. The antibodies may be polyclonal or monoclonal, and are produced by standard techniques known to one skilled in the art. The antibodies of the present invention may be employed without further change, or may be reduced to various sized fragments. The antibodies described herein may be labeled with cytotoxic agents, antibiotics, and standard detectable markers, such as chemiluminescent detection systems, radioactive labels such as $^{125}$I, and enzymes such as horseradish peroxidase, biotin, and avidin.

The antibodies provided by the present invention may be presented in kits with detectable labels and other reagents and buffers for such detection. For example, an antibody may be presented as part of a serological reagent for identification of an MHRII-AP62 protein. The labeled antibodies presented in the kits may be labeled with any standard detectable markers, such as chemiluminescent detection systems, radioactive labels such as $^{125}$I, and enzymes such as horseradish peroxidase, biotin, and avidin.

The present invention further provides a method of detecting the presence of an MHRII-associated protein in a biological sample comprising contacting the sample with an antibody immunoreactive with the MHRII-AP62 protein and detecting the antibody bound to the protein. The MHRII-associated protein may be detected in biological samples such as body fluids and cell culture. The presence of and the level of the MHRII-associated protein may be determined using the antibody immunoreactive with MHRII-AP62 protein by procedures known in the art including, but not limited to, immunoblotting, immunoprecipitation, solid phase radioimmunoassay (e.g. competition RIAs, immobilized antigen or antibody RIAs, or double antibody RIAs), enzyme-linked immunoabsorbant assay, and the like. In one embodiment of the invention, the antibody immunoreactive with the MHRII-AP62 protein may be used to determine the location of the MHRII-AP62 protein in a cell.

The present invention provides a purified and isolated nucleic acid encoding a MHRII-AP62 protein. As used herein, the nucleic acid may be genomic DNA, cDNA, RNA or antisense RNA and includes nucleic acid derived from any species, e.g., human, rat, and mouse. Due to the degeneracy of the genetic code, the nucleic acid of the present invention also includes a multitude of nucleic acid substitutions which will encode MHRII-AP62. The nucleic acid from the mouse preferably encodes the amino acid sequence for MHRII-AP62 as shown in FIG. 7B, and more preferably comprises the nucleotide sequence as shown in FIG. 7A. Even more preferably, the nucleic acid from the mouse encodes the amino acid sequence for MHRII-AP62 as shown in FIG. 8B, and more preferably comprises the nucleotide sequence as shown in FIG. 8A. The nucleic acid from the human preferably encodes the amino acid sequence for MHRII-AP62 as shown in FIG. 9B, and more preferably comprises the nucleotide sequence as shown in FIG. 9A. The present invention also includes nucleic acid sequences that are at least 80%, preferably at least 85%, more preferably at least 90%, and most preferably at least 95%, homologous with each of the nucleic acid sequences set forth above.

In order to determine the full length nucleic acid sequence encoding the MHRII-AP62 protein, oligonucleotide probes designed from the partial cDNA sequence encoding the MHRII-AP62 protein, which are described herein, may be used to isolate a full length cDNA from a cDNA library. The mouse cDNA sequences may be used as probes for screening a human cDNA library in order to obtain the sequence encoding the human homologue of the protein. The oligonucleotide probes may be obtained from a commercial source (Genset, Genelink, Perkin-Elmer, or other sources), and may be labeled with $^{32}$p using methods commonly known to those skilled in the art. The cDNA libraries may be obtained from a commercial source (Clontech) and are plated onto an appropriate membrane (nitrocellulose or Nytran, Scheicher and Schuell; Genescreen, DuPont/NEN). The cDNA libraries may be, for example, human, rat or mouse cDNA libraries. The membrane is hybridized with the labeled oligonucleotide probe, the unbound probe is removed by washing, and then the cDNA hybridizing with the oligonucleotide is detected using an appropriate method, many of which are known to one skilled in the art. The bacterial colony or bacteriophage plaque corresponding to the cDNA on the membrane is recovered, amplified, and rescreened as described above, until a single colony or plaque that hybridizes to the oligonucleotide is obtained.

The full length nucleotide sequence encoding MHRII-AP62 may also be obtained using the two-hybrid method as described in Vojtek, et al. (1993) *Cell* 74:205–214.

The cDNA clone, obtained using any of the methods described above, is then sequenced using the standard dideoxynucleotide method, known to one of skill in the art. The amino acid sequence may then be deduced from the nucleotide sequence, based upon the genetic code.

Alternatively, the full length nucleic acid sequence encoding the MHRII-AP62 protein is determined by deducing the nucleic acid sequence from the amino acid sequence, preparing an oligonucleotide, and screening a cDNA library. The protein is first isolated by isolation and purification methods such as high performance liquid chromatography (HPLC) with reverse phase columns, ion exchange columns, and gel filtration columns. Methods by which the MHRII-AP62 protein may be sequenced are known to one of skill in the art and include methods such as the Edman degradation procedure and various mass spectrophotometer procedures.

The nucleic acid sequence encoding the MHRII-AP62 protein can be prepared several ways. For example, it can be prepared by isolating the nucleic acid sequence from a natural source, or by synthesis using recombinant DNA techniques. In addition, mutated nucleic acid sequences encoding the MHRII-AP62 protein can be prepared using site mutagenesis techniques. The amino acid sequences encoded by the MHRII-AP62 nucleic acid sequence may also be synthesized by methods commonly known to one skilled in the art (*Modern Techniques of Peptide and Amino Acid Analysis,* John Wiley & Sons (1981); M. Bodansky, *Principles of Peptide Synthesis,* Springer Verlag (1984)). Examples of methods that may be employed in the synthesis of the amino acid sequences, and mutants of these sequences include, but are not limited to, solid phase peptide synthesis, solution method peptide synthesis, and synthesis using any of the commercially available peptide synthesizers. The amino acid sequences, and mutants thereof, may contain coupling agents and protecting groups used in the synthesis of the protein sequences, and are well known to one of skill in the art.

The present invention also provides a vector comprising a nucleic acid encoding a MHRII-AP62 protein, as well as a cell stably transformed with the vector. The vector may be any plasmid, viral-derived nucleic acid, lytic bacteriophage derived from phage lambda, cosmid, filamentous single-stranded bacteriophage such as M13, and the like, for cloning the MHRII-AP62 nucleic acid or introducing the nucleic acid into a cell for expression. The cell may be eukaryotic or prokaryotic. Suitable host cells include, but are not limited to, bacterial cells such as *E. coli, Bacillus subtilis, Agrobacterium tumefaciens, Bacillus megaterium,* eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator,* cultured insect cells, cultured chicken fibroblasts, cultured hamster cells, cultured human cells such as HT1080, MCF7, 143B and cultured mouse cells such as EL4 and NIH3T3 cells. Such expression systems may be used to produce a MHRII-AP62 protein by culturing a cell transformed with a vector comprising a nucleic acid encoding the MHRII-AP62 protein, and recovering recombinant MHRII-AP62 protein from the culture.

The present invention also provides single-stranded nucleic acid probes and mixtures thereof for use in detecting the presence of a nucleic acid encoding the MHRII-AP62 protein. The nucleic acid probes may be DNA, cDNA, or RNA, and are prepared from the nucleic acid sequence encoding the MHRII-AP62 protein. The probes may be the full length sequence, or fragments thereof. Typical probes are 12 to 40 nucleotides in length. Generally, the probes are complementary to the gene coding sequences, although probes to introns are also contemplated. The probes may be synthesized using an oligonucleotide synthesizer, and may be labeled with a detectable marker such as fluorescence, enzyme or radiolabeled markers including $^{32}$p and biotin, and the like. Combinations of two or more labeled probes corresponding to different regions of the nucleic acid sequence also may be included in kits to allow for the detection and/or analysis of the nucleotide sequence encoding the MHRII-AP62 protein.

The present invention further provides agents that prohibit the MHRII-AP62 protein from binding to MHRII. The agents may inhibit the binding of the MHRII-AP62 protein to the MHRII binding domain by mimicking the binding capabilities of the MHRII-AP62 protein, thereby preventing the binding of the MHRII-AP62 protein to MHRII. The agent, when bound to the MHRII binding domain, directly affects the deregulation of Myc, thereby affecting the occurrence and progression of many different types of cancers and benign proliferation disorders characterized by an abnormal proliferation of cells. Even where Myc deregulation is not the principle genetic lesion in the cancer, many cancer-associated lesions affecting signal pathways that feed into Myc and require Myc function in order to maintain the malignant phenotype. Thus, targeting the actions of Myc oncoprotein by preventing the binding of Myc-associated proteins to the Myc homology region II can potentially have a significant impact on a wide variety of human cancers. In one embodiment of the invention, the physical structure of the MHRII-AP62 protein complexed with MHRII is analyzed and agents which mimic the binding action of the MHRII-AP62 protein are designed based on this physical structure.

Also provided by the present invention are agents which inhibit the activity of the MHRII-AP62 protein by directly binding to the MHRII-AP62 protein itself. These agents prevent the MHRII-AP62 protein from binding to MHRII, thus inhibiting Myc-mediated malignant transformation. Agents that bind to the MHRII-AP62 protein may be stereochemically designed so that, based upon the structure of the MHRII-AP62 protein, they will bind to the protein and inhibit activity.

Alternatively, the agents provided by the present invention may be nucleic acid sequences or proteins that directly bind to the amino acid sequence or the nucleic acid sequence of the MHRII-AP62 protein and thereby affect transcription or translation of the sequence, ultimately inhibiting or altering the activity of the MHRII-AP62 protein and its ability to bind to MHRII.

The agents of the present invention may comprise proteins, polypeptides, peptides, nucleic acid sequences, small non-peptide organic molecules, and organic reagents. The nucleic acid sequences may comprise, for example, RNA, antisense RNA, double stranded RNA, RNA-DNA hybrids, double stranded DNA, nucleotides, oligonucleotides, or antisense oligonucleotides. The antisense nucleic acid sequences are engineered to act on the mRNA of the nucleic acid sequence encoding the MHRII-AP62 protein, preventing the nucleic acid sequence from being translated into the MHRII-AP62 protein.

Further provided by the present invention is a method of treating cancer by preventing the occurrence of and inhibiting the progression of many different types of cancers and benign proliferation disorders by administering to a subject an effective amount of the agents described herein to treat the cancer. Non-limiting examples of cancers that can be treated using the agents provided by the present invention include Burkitt's lymphoma, neuroblastoma, osteosarcoma, ovarian cancer, breast cancer, leukemia, lung cancer, colorectal cancer and prostate cancer. Non-limiting types of benign proliferation disorders that are characterized by an abnormal proliferation of cells include autoimmune diseases such as lupus, rheumatoid arthritis and psoriasis.

The present invention is described in the following Experimental Details Section, which is set forth to aid in an understanding of the invention, and should not be construed to limit in any way the invention as defined in the claims which follow thereafter.

Experimental Details Section

Derivation of the Two-Hybrid MHRII-A&P62 cDNA

To identify proteins that associate with MHRII, a modified version of the yeast two-hybrid screen method (Vojtek, et al. (1993) *Cell* 74:205–214; Schreiber-Agus, et al. (1995) *Cell* 80:777–786) developed by Fields and Song (*Nature* 340:245–246 (1989)) was employed. Standard manipulations of yeast were performed essentially as described in Schreiber-Agus, et al. (1995) *Cell* 80:777–786. A non-transactivating MHRII bait was constructed for use in the yeast two-hybrid screen. A HeLa cDNA activator library yielded several candidate clones. A partial cDNA of one of these MHRII interacting clones designated MHRII-AP62 was analyzed.

Preparation of the MHRII bait (fusion plasmid)

PCR (polymerase chain reaction) was performed on the mouse c-myc gene using the following oligonucleotides:

~PG1: 5' TgA TgA CCg AAT TCC TTg gAg gAg 3' (SEQ ID NO:1)

~RD335: 5' CCA gCT Tgg Cag Cgg CTg Ag 3' (SEQ ID NO:2)

An EcoRI site was created at the 5' end and a PstI site at the 3' end. The fragment was subcloned into the pBTM116 vector (from P. Barte and S. Fields, SUNY Stony Brook) and introduced into the yeast strain *S. cerevisiae* L40 (from S. Hollenberg, Seattle, Wash.). The fusion plasmid produces a fusion protein consisting of amino acid #104 (E) to amino acid #140 (A) of c-Myc fused to the LexA DNA binding domain. A mouse T cell lymphoma cDNA library in the pACT vector (Clontech) (generates fusion to the transactivation domain) was introduced into the L40 yeast strain expressing the MHRII bait.

In vitro Transcription/Translation Experiments of MHRII-AP62

The in vitro transcription/translation experiments of MHRII-AP62 (TNT, Promega) were performed. (See FIG. 1) The entire two hybrid derived cDNA produces a protein of ~45 kDa. The anti-sense construct and the empty vector were included as negative controls, while TBP served as a positive control. MR #62 1, 2, and 3 are from separate batches of the same reaction parameters.

The in vitro transcription/translation reactions were performed using a TNT kit (Promega) as stated below:

| | | |
|---|---|---|
| TNT rabbit reticulocyte lysate | | 25 μl |
| TNT reaction buffer | | 2 μl |
| T7 RNA polymerase | | 1 μl |
| Amino acid mixture minus methionine, 1 mM | | 1 μl |
| $^{35}$S-methionine (1,000 Cl/mmol) at 10 mCl/ml) | | 4 μl |
| Rnasin ribonuclease inhibitor (40 u/μl) | | 1 μl |
| DNA substrate | | |
| Nuclease-free $H_2O$ to final volume | | 50 μl |
| 1 μg pGEM-37-TBP: | reaction performed for 60 min. (3 tubes) | |
| 0.5 μl pRSET-AP62 | reaction performed for 90 min. (3 tubes) | |
| 1 μg $pRSET_c$ | reaction performed for 90 min. (1 tube) | |
| 1 μg $pRSET_c$: AP62 (antisense) (from miniprep) | reaction performed for 90 min. (1 tube) | |

2 μl of each reaction was removed and added 2 μl of 2×SDS loading buffer and boiled for 5 min. and analyzed on a 15% SDS-PAGE. The remainder was frozen in dry ice and stored at −70° C.

GST Pull Down Assays

CST pull down assays were performed using the $^{35}$S, IVT product of AP62 with GST alone, GST-MYC (a.a.1-204), GST-12S E1A or GST-13S E1A. (See FIGS. 2 and 3) AP62 clearly associates with both E1As and MYC, but not GST. 0.5 M NaCl was used in these washes, so the AP62-MYC in vitro interaction is a very strong one. TBP was used as a positive control for binding to GST-MYC and was generated by in vitro transcription/translation as well.

Zoo Blot

Human, mouse, xenopus and zebra fish DNAs were probed with the entire two-hybrid derived fragment of AP62. The results are presented in FIG. 4, and show that the mouse AP62 probe readily cross hybridizes with sequences in the human genome under low-stringency conditions only.

Northern Blots

Northern blots were performed using AP62 as a probe and mouse RNAs from different embryonic developmental stages and from different tissues in adults and newborns as described in Sambrook, et al. (1989) Molecular Cloning: A Laboratory Manual. CSH Laboratory; Cold Spring Harbor. The results are shown in FIGS. 5 and 6. The single ~5.2 kb mRNA transcript of the MHRII-AP62 protein is seen, and appears to be up-regulated steadily from stages 9.5 to 15.5. The highest levels of expression are seen in thymus and spleen. The expression of MHRII-AP62 in brain and kidney correlates with Myc expression.

Analysis of Partial cDNA Clone

The partial sequence for the cDNA of MHRII-AP62 and its corresponding deduced amino acid sequence were determined and are shown in FIGS. 7A and 7B. The analysis of the partial cDNA of the MHRII-AP62 clone revealed: (1) no sequence homology to any protein in eukaryotic genome databases, (2) direct interaction between MHRII or E1a and MHRII-AP62 in GST pull-down assays, and (3) broad tissue distribution of MHRII-AP62 mRNA.

Isolation and Analysis of Full cDNA Clone

A cDNA 5' probe was generated from the partial mouse cDNA of FIG. 7A and was used to isolate a full length cDNA from a mouse lid embryo 5' stretch cDNA library (Clontech). The sequence for the isolated cDNA of MHRII-AP62 and its corresponding deduced amino acid sequence were determined and are shown in FIGS. 8A and 8B.

Isolation and Analysis of Human cDNA Clone

The human cDNA clone was isolated by sequence comparison of the mouse MHRII-AP62 sequence with the database. A number of different human EST clones aligned with the murine sequence. One of the EST clones (GeneBank Accession No. AI798977) was obtained and fully sequenced. The full sequence and its corresponding deduced amino acid sequence are shown in FIGS. 9A and 9B.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A purified and isolated nucleic acid encoding the amino acid sequence set forth in SEQ ID NO:8.

2. The nucleic acid of claim 1 having the nucleotide sequence of SEQ ID NO:7.

* * * * *